United States Patent [19]

Brynes et al.

[11] Patent Number: 5,101,015
[45] Date of Patent: Mar. 31, 1992

[54] REAGENTS FOR AN AMPHETAMINE-CLASS FLUORESCENCE POLARIZATION IMMUNOASSAY

[75] Inventors: Paul J. Brynes, Libertyville; Donald D. Johnson, Lindenhurst; Cynthia M. Molina, Deerfield; Charles A. Flentge, Lake Villa; Patrick F. Jonas, Waukegan, all of Ill.

[73] Assignee: Abbott Laboratories, Abbott Park, Ill.

[21] Appl. No.: 335,627

[22] Filed: Apr. 10, 1989

[51] Int. Cl.$^5$ ................. G01N 33/536; C09K 11/06
[52] U.S. Cl. ............... 530/363; 252/301.16; 252/301.18; 436/501; 436/56; 436/901
[58] Field of Search .............. 530/405, 406, 363; 436/546, 172, 805, 816, 501, 56, 808, 901, 536; 252/301.16; 422/61

[56] References Cited

U.S. PATENT DOCUMENTS

| | | |
|---|---|---|
| 3,690,834 | 9/1972 | Goldstein et al. |
| 3,704,282 | 11/1972 | Spector |
| 3,817,837 | 6/1974 | Rubenstein et al. |
| 3,856,469 | 12/1974 | Schneider et al. |
| 3,878,187 | 4/1975 | Schneider et al. |
| 3,940,475 | 2/1976 | Gross |
| 3,966,764 | 6/1976 | Goldstein et al. |
| 3,996,344 | 12/1976 | Gross |
| 4,016,146 | 4/1977 | Soares |
| 4,022,878 | 5/1977 | Gross |
| 4,041,076 | 8/1977 | Avenia et al. |
| 4,067,774 | 1/1978 | Rubenstein et al. |
| 4,097,586 | 6/1978 | Gross |
| 4,122,078 | 10/1978 | Yoshioka et al. |
| 4,255,329 | 3/1981 | Ullman |
| 4,329,281 | 5/1982 | Christenson et al. |
| 4,351,760 | 9/1982 | Khanna et al. |
| 4,420,568 | 12/1983 | Wang et al. |
| 4,476,228 | 10/1984 | Huckzermeier et al. |
| 4,476,229 | 10/1984 | Fino et al. |
| 4,481,136 | 11/1984 | Khanna et al. |
| 4,492,762 | 1/1985 | Wang et al. |
| 4,510,251 | 4/1985 | Kirkemo et al. |
| 4,585,862 | 4/1986 | Wang et al. |
| 4,588,697 | 5/1986 | Khanna et al. |
| 4,593,089 | 6/1986 | Wang et al. |
| 4,681,859 | 7/1987 | Kramer |
| 4,751,190 | 6/1988 | Chiapetta et al. |
| 4,785,080 | 11/1988 | Farina et al. ............ 530/405 |
| 4,868,132 | 9/1989 | Brynes et al. |

FOREIGN PATENT DOCUMENTS

| | | |
|---|---|---|
| 0199042 | 10/1986 | European Pat. Off. |
| 0201751 | 11/1986 | European Pat. Off. |
| 0254120 | 2/1987 | European Pat. Off. |
| 0218010 | 4/1987 | European Pat. Off. |
| 0240021 | 10/1987 | European Pat. Off. |
| 0279213 | 8/1988 | European Pat. Off. |
| 2100744 | 6/1971 | France |
| 2111476A | 7/1983 | United Kingdom |

OTHER PUBLICATIONS

"The Radioimmunoassay of Methamphetamine" Inayama, Seiichi et al., Chem. Pharm. Bull. 25(4), 840–842 (1977).

"A New Synthesis of Dihydromancunine," Inayama, Seiichi et al., Chem. Pharm. Bull. 25(4), 847–844 (1977).

Shipchandler, M. T., et al., "4'-[Aminomethyl]fluorescein and Its N-Alkyl Derivatives: Useful Reagents in Immunodiagnostic Techniques", Analytical Biochemistry, 162:89–101 (1987).

Halfman, et al., "Homogeneous, Micelle Quenching Fluoroimmunoassay for Detecting Amphetamines in Urine", Clinical Chemistry, 32/9, 1677–1681 (1986).

"Single-Reagent Polarization Fluoroimmunoassay for Amphetamine in Urine", Chemical Abstracts, vol. 103, Aug. 26, 1985, p. 8, Abstract No. 64284y.

Eremin, S. A., et al., "Single-Reagent Polarization Fluoroimmunoassay of Methamphetamine in Urine," Clinical Chemistry, 33(10):1903–1906 (1987).

Colbert, D. L., "Single-Reagent Polarization Fluoroimmunoassay for Amphetamine in Urine," Clinical Chemistry, 31(7):1193–1195 (1985).

Cheng, L. T., "Amphetamines: New Radioimmunoassay," FEBS Letters, 36(3), Nov. 1973.

Riceberg, Louis J., et al., "Estimation of $\beta$-3,4-Dimethoxyphenethylamine and Related Compounds in Urine Extracts by Radioimmunoassay," Biochemical Pharmacology, vol. 25, 259–265 (1975).

Faraj, Bahjat A., "Specificity of an Antibody Directed Against d-Methamphetamine Studies with Rigid and Nonrigid Analogs," Journal of Medicinal Chem. 19:1 (1976).

Molina, C., et al., "An FPIA Specific for Amphetamine and Methamphetamine," Clinical Chemistry, 31:6, 941–942 (1985).

Kanda, Yukio, et al., "Studies on Immunoassay for Methamphetamine", Japanese Publication 31:3 (1978).

Riceberg, Louis J. et al., "radioimmunoassays of 3,4,5—

(List continued on next page.)

Primary Examiner—David L. Lacey
Assistant Examiner—Thomas E. Daley
Attorney, Agent, or Firm—Roberta L. Hastreiter; Priscilla E. Porembski; Thomas M. Breininger

[57] ABSTRACT

A fluorescence polarization immunoassay (FPIA) for detecting the presence of one or more amphetamine-class analytes in a test sample is provided. The immunoassay uses competition between the analyte and a fluorescently labeled tracer for the binding site on an antibody specific for phenethylamine derivatives. The concentration of amphetamine-class analyte in the sample determines the amount of tracer that binds to the antibody. The amount of tracer/antibody complex formed can be quantitatively measured and is inversely proportional to the quantity of analyte in the test sample. The invention relates to tracers, to immunogens used to elicit antibodies for use as assay reagents, and to assay kits incorporating these tracers and assay reagents.

9 Claims, No Drawings

OTHER PUBLICATIONS

Trimethoxyphenethylamine(Mescaline) and 2,5-Dimethoxy-4-Methylphenyl-isopropylamine (DOM)," Analytical Biochemistry 60:551-559 (1974).

Aoki, Kimiko, et al., "A Screening Method for Urinary Methamphetamine—Latex Agglutination Inhibition Reaction Test," Forensic Science International, 27 pp. 49-56, (1985).

Tokura, Seichi, et al., "Induction of Methamphetamine-Specific Antibody Using Biodegradable Carboxymethyl-Chitin," Analytical Biochemistry 161:117-112 (1987).

Tamaki, Yoshihiro, et al., "Solid-Phase MicroELISA for Methamphetamine," Jpn. J. Legal Med. 37:4, 417-420 (1983).

Ishiyama, Ikuo, et al., "Histochemical Demonstration of Methamphetamine by Immunocytochemistry," Journal of Forensic Science, 32:3 658 (1987).

Yuzuriha, Teruaki, et al., "Preparation of a Specific Antibody to Methamphetamine," Chem. Pharm. Bull., 25:4, 840 (1977).

Budd, Robert D., "Amphetamine EMIT-Structure Versus Reactivity," Clinical Toxicology, 18:1, 91-110 (1981).

Budd, Robert D., "Amphetamine Radioimmunoassay-Structure Versus Reactivity," 18:3, 299-316 (1981).

"An Improved Label for Amphetamine Fluoroimmunoassay," Therapeutic Drug Monitoring 11:607-611 (1989).

Tillotson, J. A., et al., "Fluorometric Apoprotein Titration of Urinary Riboflavin," Anal. Biochemistry, 107, 214-219 (1980).

Rhodes, M. B., et al., "The Flavoprotein-Apoprotein System of Egg White," J. Biol. Chemistry, 234, No. 8, 2054-2060 (1959).

Nishikimi et al., "Flavin-Protein Interaction in Egg White Flavoprotein," J. Biochem. 73, 1233-1242 (1972).

Murthy, U. S., et al., "The Interaction of Riboflavin with a Protein Isolated from Hen's Egg White: A Spectrofluorimetric Study," Biochemica et Biophysica Acta, 434, 69-81 (1976).

REAGENTS FOR AN AMPHETAMINE-CLASS FLUORESCENCE POLARIZATION IMMUNOASSAY

BACKGROUND OF THE INVENTION

1. Field of the Invention

This invention relates to a method and reagents for detecting amphetamine-class drugs in a test sample such as urine. In particular, the invention relates to a fluorescence polarization immunoassay procedure for determining the presence or amount of amphetamine-class drugs in a test sample, to a novel class of tracer compounds used as reagents in such procedures, and to immunogen compounds used to raise antibodies for use in such procedures.

2. Description of Related Art

Amphetamine-class drugs are sympathomimetic phenethylamine derivatives having central nervous system stimulant activity. These drugs have been used for the treatment of obesity, narcolepsy and hypotension. Excessive use of these drugs, however, may lead to tolerance and physical dependence, and because of their stimulant effects the drugs are commonly abused. Physiological symptoms often associated with very high amounts of ingested amphetamine-class drugs include elevated blood pressure, dilated pupils, hyperthermia, convulsions and acute amphetamine psychosis.

The biological fluid used most frequently for detecting or quantitating amphetamine-class drugs is urine. Other biological fluids, however, such as serum, plasma or saliva might be used as test samples. In the past, amphetamines have been detected by a number of techniques including thin-layer chromatography (TLC), gas chromatography (GC) and high performance liquid chromatography (HPLC). These methods generally involve complicated chemical extractions of the drugs from the test sample, procedures which require trained personnel and lengthy assay times.

Binding assays are a preferred alternative to the chemical methods such as GC, TLC and HPLC for the detection of analytes. Binding assays for detecting antigens and antibodies depend upon the immunological reactivity which characterizes these substances. Generally, these assays are collectively termed immunoassays.

Immunoassay techniques take advantage of the mechanisms of the immune systems of higher organisms, wherein antibodies are produced in response to the presence of antigens which are pathogenic or foreign to the organisms. One or more antibodies are produced in response to and are reactive with a particular antigen, thereby creating a highly specific reaction mechanism which can be used in vitro to determine the presence or concentration of that particular antigen in a biological sample.

Competitive binding immunoassays for measuring analytes of interest are based on the competition between the analyte in the test sample and a labeled reagent (i.e., tracer) for a limited number of binding sites on a binding member (e.g., an antibody) that is specific for both the analyte and tracer. Generally, the concentration of analyte in the sample determines the amount of tracer that will bind to the antibody. The amount of tracer/antibody complex produced can be quantitatively measured and is inversely proportional to the quantity of analyte in the test sample.

Fluorescence polarization provides a means for measuring the amount of tracer/antibody complex produced in a competitive binding immunoassay. Fluorescence polarization techniques are based on the principle that, when excited by linearly polarized light, a fluorescently labeled reagent will rotate rapidly, and fluorescent light emitted by that rotating tracer becomes partially depolarized due to the rapid rotation. As a result, the tracer will emit fluorescence with a degree of polarization inversely related to the tracer's rate of rotation, i.e., the higher the rotation the lower the polarization of the emitted light (or the greater the depolarization of the emitted light). The speed of rotation and the amount of depolarization decrease when the tracer becomes bound to a heavier molecule, such as when it becomes bound to the comparatively heavier antibody molecule. If a reaction mixture containing a fluorescent tracer/antibody complex is excited by linearly polarized light, then the emitted light generally remains polarized because the fluorophore in the complex is constrained from rapidly rotating. When a "free" tracer (i.e., tracer that is not bound to an antibody) is excited by linearly polarized light, its rotation is much faster than that of the tracer/antibody complex, and therefore, depolarization of the emitted light is increased.

By comparing standard preparations containing known concentrations of analyte to test samples containing unknown levels of the analyte, the fluorescence polarization technique provides a quantitative means for measuring the amount of tracer/antibody complex produced in a competitive binding assay. This technique is currently being employed by Abbott Laboratories in its commercially available TDx® Therapeutic Drug Monitoring System (as described in U.S. Pat. No. 4,269,511 and U.S. Pat. No. 4,420,568) and its commercially available IMx® and ADx TM automated instruments.

As disclosed in the '511 and '568 patents, because the tracer must compete with the analyte for binding to the antibody in a fluorescence polarization immunoassay (FPIA), the tracer must possess a molecular structure sufficiently similar to the analyte so as to be recognized by an antibody specific for the analyte. For this reason the tracer is also referred to as a fluorescently labeled analyte-analog, a substantial portion of which has the same spatial and polar organization as the analyte to define one or more determinant sites capable of competing with the analyte for the binding sites on the antibody.

An accurate and reliable immunoassay for the detection or quantification of a specific amphetamine-class compound requires that antibody cross-reactivity, i.e., the recognition of compounds other than the desired analyte, be minimized. Copending U.S. Patent Application Ser. Nos. 010,355 (filed Feb. 3, 1985) and 265,361 (filed Oct. 28, 1988) disclose assay reagents and FPIA methods for quantitating amphetamine and methamphetamine in test samples while eliminating phenethylamine cross-reactivity.

To date, however, no fluorescence polarization immunoassay has been disclosed which enables the screening of a test sample for a broad range of amphetamine-class drugs. Accordingly, a need exists for providing an assay and reagents for performing an accurate and sensitive FPIA for the simultaneous detection of the presence or amount of amphetamine-class drugs.

SUMMARY OF THE INVENTION

The present invention provides a method for detecting or quantitating amphetamine-class compounds in test samples using a fluorescence polarization immunoassay technique. The method comprises the steps of:
a. contacting a test sample, suspected of containing one or more amphetamine-class compounds, to a fluorescently labeled tracer and an antibody capable of recognizing and binding the amphetamine-class compounds and the tracer, whereby binding of (i) the amphetamine-class compounds or (ii) the tracer to the antibody blocks binding of (i) the tracer or (ii) the amphetamine-class compounds, respectively, to the antibody;
b. passing plane-polarized light through the test solution to obtain a fluorescence polarization response; and
c. detecting the fluorescence polarization response as a measure of the presence or amount of amphetamine-class compounds in the test sample.

The present invention further provides tracer compounds used as reagents in such a method, and immunogen compounds used to raise antibodies for use as reagents in such method. The present invention also includes kits of reagents for use in an amphetamine-class assay.

The immunogens of the present invention comprise a compound of the formula:

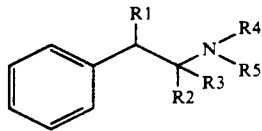

wherein at least one of R1, R2, R3, R4, and R5 is X, and when other than X are selected from H, OH or $CH_3$. X is $(M)_zWQ$ wherein Q is a carrier material; W is a coupling group selected from NH, CO, COOH, CHO, or OH, present on the carrier material; z is 0 or 1; and M is a linking group.

The tracers of the present invention comprise a compound of the formula:

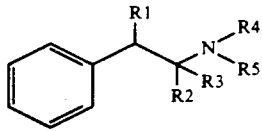

wherein at least one of R1, R2, R3, R4, and R5 is X, and when other than X are selected from H, OH or $CH_3$. X is MFI wherein FI is a fluorescent material and M is a linking group.

DETAILED DESCRIPTION OF THE INVENTION

Amphetamine-class drugs include derivatives and isomers of substances which are related structurally and pharmacologically to phenethylamine and which duplicate the action of amphetamine to various degrees. The amphetamine-class drugs can be grouped into at least five major classes, based upon their therapeutic usage, including: 1) sympathomimetic drugs, e.g.s, amphetamine and methamphetamine; 2) anorexigenic drugs, e.g.s, phentermine and fenfluramine; 3) antidepressants, e.g., tranylcypromine; 4) decongestants, e.g.s, ephedrine and phenylpropanolamine; and 5) methoxylated hallucinogens, e.g.s, 3,4-methylenedioxyamphetamine and N-ethyl-3,4-methylenedioxyamphetamine.

The present invention provides reagents and a semi-quantitative assay enabling the detection of such potentially abused drugs as well as the determination of overdoses of over-the-counter diet and cold relief products. The reagents of the present invention are intentionally cross-reactive to enable the performance of an amphetamine-class assay, i.e., the screening of a test sample for a broad range of amphetamine-class drugs. The reagents of the present invention can also be used in combination with tracers and antibodies for other drugs to provide a multi-analyte assay for a plurality of abused substances.

DEFINITIONS

The following definitions are applicable to the present invention.

The term "determinants", as used herein, refers to those regions of the antigen involved in specific binding reactions which are typified by the immunoreactive binding of antigens and antibodies. In essence, it is the determinants which differentiate antigens, and therefore antibodies, from one another on the basis of immunological specificity.

The term "analyte", as used herein, refers to a molecule for which a binding member, such as an antibody, can be obtained or formed. The analytes of interest in the present invention are amphetamine-class drugs that can be generally represented by the following phenethylamine formula:

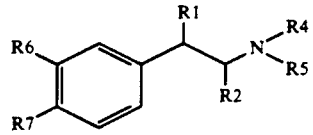

wherein: R1 is H or OH; R2 through R5 are independently H, $CH_3$, $C_2H_5$ or benzyl; and R6 and R7 are independently hydrogen, chloro, methyl, hydroxy or methoxy groups, or which together form a methylenedioxy bridge. The analytes of interest are haptens from which antigens, i.e., immunogens are to be made. "Hapten" refers to a protein-free compound, generally of low molecular weight, which does not itself elicit antibody formation, but which does elicit the immune response when coupled to an immunogenic carrier.

The term "analyte-analog", as used herein, refers to a molecule which contains substantially the same spatial and polar organization as one or more determinant sites of the analyte of interest. This duplication of the determinant(s) enables the analyte-analog to compete with the analyte in the test sample for a binding site on an analyte-specific binding member, such as an antibody. In addition, the analyte-analog can be modified such that it is not identical to the analyte but retains the necessary determinant(s) for binding to an analyte-specific binding member, i.e., it is sufficient that the analyte-analog substantially duplicate the appropriate determinant(s). Therefore, the analyte-analog can be any molecular structure which contains chemical groups, amino acids, or nucleotides different from those of the analyte and/or which contains fewer chemical groups, amino acids, or nucleotides than the analyte, so long as that analyte-analog substantially duplicates the analyte determinant such that a specific binding member will recognize and bind to that substantially duplicated determinant.

The term "immunogen", as used herein, refers to a substance capable of eliciting an immune response, i.e., capable of eliciting the production of antibodies in a host animal to which the immunogenic substance is administered. The immunogens of the present invention especially refer to an analyte or analyte-analog which is attached to a carrier conferring antigenicity.

The term "carrier", as used herein, refers to a substance capable of conferring antigenicity; the carrier will typically be antigenic itself, although it may be an incomplete antigen, becoming complete only when coupled to the hapten. The carrier material can be a natural or synthetic substance, provided that it is an antigen or a partial antigen and that it has one or more functional moieties by means of which it can be coupled. For example, the carrier material can be a protein, a glycoprotein, a nucleoprotein, a polypeptide, a polysaccharide, a lipopolysaccharide or a poly (amino acid). An example of an apparently incomplete antigen is the polypeptide, glucagon. Specific examples of such natural protein carriers are bovine serum albumin (BSA), keyhole limpet hemocyanin, egg ovalbumin, bovine gamma-globulin, thyroxine binding globulin and human immunogamaglobulin. Exemplary of the synthetic carrier is a poly(amino acid), polylysine. In practice, a single carrier material can have a plurality of hapten moieties coupled to it. Subject to steric hindrance, the maximum number will be determined by the number of reactive coupling groups on the carrier material.

The term "tracer", as used herein, refers to an analyte or analyte-analog which is attached to a fluorescent substance. The fluorescent substance is the detectable component of the tracer reagent.

In accordance with the method of the present invention, a test sample suspected of containing one or more analytes of interest is intermixed with a tracer and an antibody specific for the analytes and the tracer. Any analyte present in the sample completes with the tracer for the limited number of binding sites on the antibody, resulting in the formation of analyte/antibody and tracer/antibody complexes. By maintaining the concentration of tracer and antibody at a constant level, the ratio of analyte/antibody complex to tracer/antibody complex that is formed is directly proportional to the amount of analyte present in the sample.

By exciting the mixture with polarized light and measuring the polarization of the fluorescence emitted by free tracer and tracer/antibody complex, one is able to determine quantitatively the amount of analyte in the sample. A tracer which is not complexed to an antibody is free to rotate in less than the time required for absorbtion and re-emission of fluorescent light. As a result, the re-emitted light is relatively randomly orientated so that the fluorescence polarization of a tracer not complexed to an antibody is low. Upon complexing with a specific antibody, the tracer assumes the rotation of the antibody molecule, which is slower than that of the relatively smaller tracer molecule, thereby increasing the polarization of the re-emitted light. Therefore, when an analyte competes with the tracer for antibody sites, the observed polarization of fluorescence of the tracer/antibody complex becomes a value somewhere between that of the tracer and the tracer/antibody complex. If the sample contains a high concentration of the analyte, the observed polarization value is closer to that of the free tracer, i.e., low. If the sample contains a low concentration of the analyte, the polarization value is closer to that of the bound tracer, i.e., high. By sequentially exciting the reaction mixture of an immunoassay with vertically and then horizontally polarized light, and analyzing only the vertical component of the emitted light, the polarization of the fluorescence in the reaction mixture can be accurately determined. The precise relationship between polarization and concentration of the analyte to be determined is established by measuring the polarization values of calibrators having known concentrations. The concentration of the analyte can be interpolated from a standard curve prepared in this manner.

The immunoassay according to the invention is referred to as a homogenous assay, which means that the end polarization readings are taken from a solution in which bound tracer is not separated from free tracer. This is a distinct advantage over heterogenous immunoassay procedures, wherein the bound tracer must be separated from the free tracer before a reading can be taken.

REAGENTS

The analyte or analyte-analog provide the basic template for the tracer reagent as well as the immunogen used to elicit the antibodies for the assay. The analyte or analyte-analog is attached to a carrier to form the immunogen or to a detectable label to form the tracer.

In the present invention, both the immunogens used to elicit antibodies and the tracer reagents can be represented by the following general structural formula which is similar to the analyte structure described above:

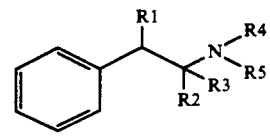

Generally, R1 is H or OH and R2 through R5 are independently H, $CH_3$, $C_2H_5$ or benzyl, but when at least one of the R groups is or includes a carrier material, the structure represents the immunogen used to elicit antibodies which are used in the assay. Alternatively, when at least one of the R groups is or includes a fluorescent material, the structure represents the tracer.

An objective of the present FPIA is to have competition between the tracer reagent and any amphetamine-class drugs which may be present in the test sample for the antibody reagent. Many variations in the structure of the immunogens and tracers are allowed in achieving this goal.

1. ANTIBODIES

The antibodies used in the present invention are prepared by developing a response in a host animal to one of the immunogens described below. The immunogens comprise a carrier attached to an analyte or analyte-analog. The carrier is a macromolecule which confers antigenicity to the analyte or analyte-analog thereby enabling the production of antibodies which are specific for both the tracer and a plurality of amphetamine-class drugs. The immunogen is administered and the appropriate antibodies are selected according to methods well-known to those skilled in the art. It should be understood that although rabbits and sheep were the immune hosts used in the experiments detailed herein, any in vivo or in vitro host capable of producing antibodies to the structures can be used. The resulting antibodies bind to the amphetamine-class drugs in the test sample as well as to the analyte or analyte-analog component of the tracer.

a. The Structure of the Immunogens

Immunogens can be produced from a wide variety of phenethylamine derivatives. The novel immunogens of the present invention have the general structural formula presented above. Typically, a poly(amino acid) carrier is attached to the phenethylamine derivative by a linking group at one of the R positions. In preferred forms of the invention, the immunogen can be represented by the following general structure:

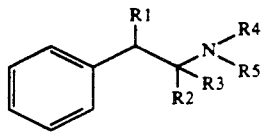

wherein at least one of R1, R2, R3, R4, and R5 is X, and when other than X are independently selected from the group consisting of H, OH and CH$_3$;

X is (M)$_z$WQ wherein:

Q is the carrier material;

W is a coupling group selected from the group consisting of NH, CO, COOH, CHO, and OH, present on the carrier material;

M is a linking group consisting of from 0 to 15 carbon atoms and heteroatoms, including not more than six heteroatoms, arranged in a straight or branched chain, saturated or unsaturated, with the proviso that not more than two heteroatoms are linked in sequence and that branchings may occur only on carbon atoms; and z is zero or one, i.e., in certain instances there is no linking arm present and z=0, When M involves only carbon atoms, it is preferred that M is from 1 to 10 carbon atoms. Suitable heteroatoms include nitrogen, oxygen, sulfur, silicon and phosphorus. For example, where M includes nitrogen and oxygen as heteroatoms, M can be —CH$_2$CH=N—O—CH$_2$—.

Exemplary immunogens, therefore, include structures wherein R5 can comprise CONH~poly(amino acid), CH$_2$CONH~poly(amino acid), CH$_2$CH$_2$CONH~poly(amino acid), or CH$_2$CH=CHCONH~poly(amino acid); or R1 can comprise OCH$_2$CONH~poly(amino acid); or R3 can comprise CONH~poly(amino acid). The most preferred form of the immunogen is N-carboxymethyl-d,l-amphetamine~bovine serum albumin having the following formula:

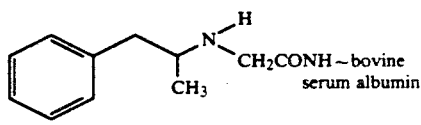

This immunogen is preferred because it elicits the best antibody response. It should be appreciated that R2 and R3 are interchangeable, as are R4 and R5. Although BSA is the poly(amino acid) carrier used in this preferred form, it should be understood that a variety of carriers, as described above, can be used.

b. The Synthesis of the Immunogens

In the immunogens of the present invention, the chemical bonds between the carboxyl group-containing phenylethylamine haptens and the amino groups on the protein carrier can be established using a variety of methods known to one skilled in the art. It is frequently preferable to form amide bonds. Amide bonds are formed by first activating the carboxylic acid moiety of the phenylethylamine hapten by reaction with a leaving group reagent (e.g., N-hydroxysuccinimide, 1-hydroxybenztriazole, p-nitrophenol and the like). An activating reagent such as dicyclohexylcarbodiimide, diisopropylcarbodiimide and the like can be used. The activated form of the phenylethylamine hapten is then reacted with a buffered solution containing the protein carrier.

In cases where the phenylethylamine hapten contains a primary or secondary amino group as well as the carboxyl group, it is necessary to use an amine protecting group during the activation and coupling reactions to prevent the hapten from reacting with itself. Typically, the amines on the hapten are protected by forming the corresponding N-trifluoroacetamide, N-tert-butyloxycarbonyl urethane (N-t-BOC urethane), N-carbobenzyloxy urethane or similar structure. Once the coupling reaction to the protein carrier has been accomplished, as described above, the amine protecting group can be removed using reagents that do not otherwise alter the structure of the immunogen. Such reagents and methods are generally known to one skilled in the art and include weak or strong aqueous or anhydrous acids, weak or strong aqueous or anhydrous bases, hydride-containing reagents such as sodium borohydride or sodium cyanoborohydride, and catalytic hydrogenation. Various methods of conjugating haptens and carriers are also disclosed in U.S. Pat. Nos. 3,996,344 and 4,016,146 which are herein incorporated by reference.

2. THE TRACERS a. The Structure of the Tracers

Like the immunogens of the present invention, the structure of the tracers of the present invention has many possible variations. The tracers can be produced from a wide variety of phenethylamine derivatives. The novel tracers of the present invention have the same basic structure as presented above, but with a fluorescent material attached to the phenethylamine derivative directly or by a linking group at one of the R positions. In preferred forms of the invention, the tracer can be generally represented by the following general structure:

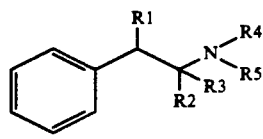

wherein at least one of R1, R2, R3, R4, and R5 is X, and when other than X are independently selected from the group consisting of H, OH and CH$_3$;

X is MFl wherein:

M is as previously described; and

Fl is the fluorescent material.

Exemplary tracers, therefore, include the structures:
wherein R5 comprises
CO-Fl,
CH$_2$-Fl,
CONH-Fl
CONHCH$_2$-Fl,
(CH$_2$)$_n$CONHCH$_2$-Fl where n=1 or 2,
CH(CH$_3$)CONHCH$_2$-Fl,
CH$_2$CON(CH$_2$CH$_3$)CH$_2$-Fl,
CH$_2$CON(CH$_2$CH$_2$CH$_2$CH$_3$)CH$_2$-Fl,
(CH$_2$)$_n$NHCO-Fl where n=1, 2 or 3, or
CH$_2$CONHCH$_2$CH$_2$NHCO-Fl; or
wherein R3 comprises
CONHCH$_2$-Fl, or
CONHCH$_2$CH$_2$NHCO-Fl; or
wherein R2 comprises
(CH$_2$)$_n$CONHCH$_2$-Fl where n=1 or 2, or
(CH$_2$)$_n$NHCO-Fl where n=1, 2 or 3; or
wherein R1 comprises
OCH$_2$CONHCH$_2$-Fl.

The most preferred tracer is N-acetamidomethyl-fluorescein-d,l-amphetamine∼Fl having the following formula:

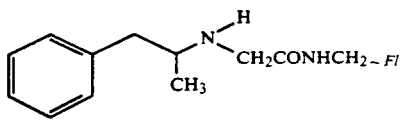

Again, it should be appreciated that R2 and R3 are interchangeable, as are R4 and R5.

The choice of the fluorescent material for labeling the analyte or analyte-analog and thereby forming the tracer is advantageously flexible and is largely up to the preferences of the practitioner. It will be readily appreciated that the fluorescent labels are ideally chosen in accordance with their size, that is, the smaller the molecule, the more rapid it can rotate, and the more effective it is as as FPIA tracer component. In the present invention, the preferred fluorescent labels are fluorescein and fluorescein derivatives. These compounds provide fluorescent response when excited by polarized light of an appropriate wavelength and thereby enable the fluorescence polarization measurement. For example, any of the following fluorescein compounds or derivatives can be used: fluorescein amine; carboxy fluorescein; alpha-iodoacetamido fluorescein; aminomethyl fluorescein; 2,4-dichloro-1,3,5-triazin-2-yl-amino fluorescein; 4-chloro-6-methoxy-1,3,5-triazin-2-yl-amino fluorescein; and fluorescein isothiocyanate. Especially preferred fluorescent substances are aminomethyl fluorescein, N-alkyl aminomethyl fluorescein and carboxy fluorescein.

Fluorescein exists in two tautomeric forms depending on the acid concentration (pH) of the environment. In the open (acid) form, the fluorescein molecule (or compound containing a fluorescein moiety) is capable of absorbing blue light and emitting green fluorescence after an excited state lifetime of about four nanoseconds. When the open and closed forms coexist, the relative concentration of molecules in the open and closed forms is easily altered by adjustment of the pH level. Generally, the tracers of the present invention are prepared in solution as biologically acceptable salts such as sodium, potassium, ammonium and the like, which allow the tracers to exist in the open, fluorescent form. The specific salt present will depend on the buffer used to adjust the pH level. For example, in the presence of sodium phosphate buffer, the tracers of the present invention will generally exist in the open form, as a sodium salt.

As used herein, the term "fluorescein", either as an individual compound or as a component of a larger complex, is meant to include both the open and closed forms, if they exist for a particular molecule, except in the context of fluorescence. An open form is necessary for the fluorescence to occur.

The particular tracers formed in accordance with the present invention have been found to produce a surprisingly good assay, as will be demonstrated in the Examples. The concentration of the analyte which can be assayed in accordance with the present invention will generally vary from about $10^{-2}$ to about $10^{-13}$M, more usually from about $10^{-4}$ to about $10^{-10}$M. Higher concentrations of analyte can be assayed upon dilution of the original sample. While the concentration range of analyte in the sample will determine the range of concentration of the reagents, i.e., tracer and antibody, the individual reagent concentrations will be determined empirically to optimize the sensitivity of the assay. Appropriate concentrations of the tracer and antibody can be ascertained by one of ordinary skill in the art.

a. The Synthesis of the Tracers

The tracers of the present invention are prepared by coupling a fluorescent material to a phenylethylamine hapten having either an amino or a carboxyl coupling group. A phenylethylamine hapten with a terminal carboxyl group can be coupled to an aminoterminal fluorescein derivative by first activating the carboxylic acid moiety of the hapten. Activation can be achieved by reacting the hapten with a leaving group reagent such as N-hydroxysuccinimide, 1-hydroxybenztriazole, p-nitrophenol and the like, with an activating reagent such as 1,3-dicyclohexylcarbodiimide. The activated hapten is then allowed to react with a basic dimethylformamide solution of the fluorescein derivative. Other activating groups, such as N,N'-disuccinimidyl carbonate and 2-ethyl-5-phenylisoxazolium-3'-sulfonate can be used.

A phenylethylamine hapten with a terminal amine can be transformed to a highly reactive N-hydroxysuccinimide urethane by reaction with N,N'-disuccinimidyl carbonate in either acetonitrile or dimethylformamide. A urea coupling to an amino-terminal fluorescein derivative is then effected by combining the haptenic urethane with the fluorescein moiety in a basic solution of dimethylformamide. An amino group-containing hapten can also be coupled to either 5-carboxyfluorescein or 6-carboxyfluorescein which has been activated with N-hydroxysuccinimide using a solvent such as dimethylformamide.

In cases where the hapten contains a primary or secondary amino group, in addition to the carboxylic acid or amine which is to be coupled, it is necessary to use an amine protecting group during the activation and coupling reactions to prevent the hapten from reacting with itself. This can be accomplished using a variety of methods known to one skilled in the art. For example, the amines on the hapten can be protected by forming the corresponding N-trifluoroacetamide, N-tert-butyloxycarbonyl urethane, N-carbobenzyloxy urethane, or similar structure. As described above, once the coupling reaction to the fluorescein derivative has been accomplished, the amine protecting group can be removed using reagents that do not otherwise alter the structure of the tracer. Such reagents and methods include weak or strong aqueous or anhydrous acids, weak or strong aqueous or anhydrous bases, hydride-containing reagents such as sodium borohydride or sodium cyanoborohydride, and catalytic hydrogenation.

3. The Assay

The novel tracers and antibodies of the present invention produce excellent results in a fluorescence polarization assay for amphetamine-class drugs. The assay of the present invention provides a rapid, semi-quantitative fluorescence polarization screening assay which can indicate the presence of one or more amphetamine-class drugs or metabolites in a test sample.

The assay is performed in accordance with the following general procedure:
1) a measured volume of standard or test sample, containing or suspected of containing one or more amphetamine-class drugs, is delivered into a test tube;
2) a known concentration of tracer is added to the tube;
3) a known concentration of analyte-specific antibody, produced using an immunogen as described above, is added to the tube;
4) the reaction mixture is incubated at room temperature, wherein the tracer and any analyte compete for the limited number of anitbody determinants, resulting in the formation of tracer/antibody and analyte/antibody complexes; and
5) the amount of tracer/antibody complex is measured by fluorescence polarization techniques to determine the presence or amount of analyte in the test sample.

Although the principles of the invention are applicable to manually performed assays, the automated nature of the TDx ® System assures minimal technician time to perform assays or interpret data. The results can be quantified in terms of "millipolarization units", "span" (in millipolarization units) and "relative intensity". The measurement of millipolarization units indicates the maximum polarization when a maximum amount of the tracer is bound to the antibody in the absence of amphetamine-class substances in the test sample. The higher the net millipolarization units, the greater the binding of the tracer to the antibody. For purposes of the present invention, a net millipolarization value of about 200 to about 280 is preferred. A value in the range of about 225 to about 250 is more preferable. And, a value of about 240 is most preferable.

The span is an indication of the difference between the net millipolarization at the points of the maximum and the minimum amounts of tracer bound to the antibody. A larger span provides for a better numerical analysis of data. For purposes of the present invention, a span within the range of about 80 to about 150 is preferred. A value in the range of about 85 to about 100 is more preferable.

The intensity is a measure of the strength or amplitude of the tracer's fluorescence signal that can be read above the background fluorescence. Thus, a higher intensity will give a more accurate measurement. The intensity is determined as the sum of the vertically polarized intensity plus twice the horizontally polarized intensity. The intensity can range from a signal of about three times to about sixty times the background noise, depending upon the concentration of the tracer and other assay variables. For the purposes of the present invention, an intensity of about thirteen to about fifty times that of background noise is preferred.

The pH at which the method of the present invention is conducted must be sufficient to allow the fluorescein moiety of the tracer to exist in its open form. The pH can range from about 3 to about 12, more usually in the range of from about 5 to about 10, and most preferably from about 6 to about 8. Various buffers can be used to achieve and maintain the pH during the assay procedure. Representative buffers include borate, phosphate, carbonate, Tris, barbital and the like. The particular buffer used is not critical to the present invention, but the Tris and phosphate buffers are preferred. The cation portion of the buffer will generally determine the cation portion of the tracer salt in solution.

Additionally, certain materials can be included in one or more assay reagents to remove any substances which might interfere with the binding of the reagents to the analyte of interest or with the detection of the fluorescent signal. For example, riboflavin binding protein (RBP) can be used in the assay to prevent fluorescent interference due to the presence of riboflavin in the test sample. Riboflavin, or vitamin $B_2$, is a common constituent of many foods and commercially available vitamin supplements. Riboflavin is excreted in urine and has a fluorescence spectrum similar to that of fluorescein. Ordinary consumption of riboflavin is unlikely to produce more than trace amounts of riboflavin in the urine, but test results using urine samples can be distored by the consumption of excessive quantities of riboflavin by persons wishing to prevent the detection of the analyte of interest.

EXAMPLES

The following examples describe methods for synthesizing the novel immunogens and tracers as well as assays which were performed in accordance with the present invention.

Synthesis of Immunogens

Example 1

N-Carboxymethyl-d,l-Amphetamine—BSA Immunogen

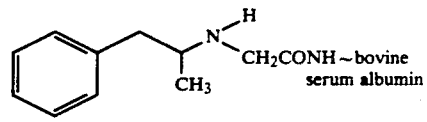

Five hundred milligrams of d,l-amphetamine sulfate (1.36 mmol) were dissolved in distilled water (20 ml), and the pH was adjusted to 13 by the addition of 1N NaOH. The basic solution was extracted four times with 20-milliliter portions of chloroform. The combined extracts were dried over anhydrous sodium sulfate, and the organic solvent was evaporated to yield a clear oil. After redissolving the residue in chloroform (20 ml) and adding ethyl bromoacetate (331 µl, 2.99 mmol), the solution was heated at reflux for 24 hours. Triethylamine (378 µl, 2.72 mmol) was added, and the solution was refluxed for an additional two hours. The reaction product was isolated by diluting the solution with ethyl acetate (30 ml), washing the solution three times with 100-milliliter portions of water and drying the combined organic extracts over anhydrous sodium sulfate. Evaporation of the solvent in vacuo yielded 509 milligrams of N-carboethoxymethyl-d,l-amphetamine as a colorless oil.

N-Carboethoxymethyl-d,l-Amphetamine (313 mg, 1.41 mmol) was dissolved in anhydrous tetrahydrofuran (2.0 ml). Di-Tert-Butyl Dicarbonate (328 µl, 2.12 mmol) and 4-N,N-dimethylaminopyridine (2.0 mg) were then added to form a reaction mixture. The reaction mixture was treated with a solution of triethylamine (217 µl, 1.56 mmol) in dimethylformamide (2.0 ml) and was stirred at room temperature for six hours. The reaction product was isolated by diluting the solution with ethyl acetate (20 ml), washing it five times with 100-milliliter portions of water and drying the organic phase over anhydrous sodium sulfate. Evaporation of the solvent in vacuo yielded 400 milligrams of N-tert-butoxycarbonyl-N-carboethoxymethyl-d,l-amphetamine as a colorless oil.

N-Tert-Butoxycarbonyl-N-Carboethoxymethyl-d,l-Amphetamine (381 mg, 1.18 mmol) was dissolved in a solution of methanol (6.0 ml) and 10% aqueous sodium hydroxide (4.0 ml). After stirring at room temperature for three hours, the basic solution was washed three times with 20-milliliter portions of chloroform. The aqueous phase was adjusted to pH 3 with 1N HCl, extracted three times with 15-milliliter portions of chloroform and then dried over anhydrous sodium sulfate. Removal of the solvent in vacuo yielded 170 milligrams of N-tert-butoxycarbonyl-N-carboxymethyl-d,l-amphetamine as a colorless oil.

Twenty-four milligrams of N-tert-butoxycarbonyl-N-carboxymethyl-d,l-amphetamine (0.083 mmol) was dissolved in anhydrous dimethylformamide (400 µl) and was then treated with a mixture of N-hydroxysuccinimide (10 mg, 0.092 mmol) and dicyclohexylcarbodiimide (19 mg, 0.092 mmol). After stirring at room temperature for six hours, additional portions of N-hydroxysuccinimide (10 mg, 0.092 mmol) and dicyclohexylcarbodiimide (19 mg, 0.092 mmol) were added, and the suspension was stirred for three hours more. At the end of this period, the suspension was filtered and added dropwise to a stirred solution of BSA (141 mg) in 0.1N phosphate buffer (3.6 ml, pH 8.0) containing methanol (400 µl). After stirring at room temperature for 18 hours, the resulting suspension was filtered and dialyzed extensively against distilled water. Lyophilization of the protein solution yielded 131 milligrams of a white powder. The tert-butoxycarbonyl group was then removed from the haptenic moiety by suspending the dry immunogen in chloroform (10 ml) and adding anhydrous trifluoroacetic acid (10 ml). The resulting clear solution was stirred at room temperature for five minutes and then evaporated in vacuo to yield a clear oily residue. A quantity of 1N NaOH sufficient to raise the pH to 11 was added, and the solution was dialyzed extensively against distilled water. Lyophilization of the protein solution yielded 202 milligrams of N-carboxymethyl-d,l-amphetamine immunogen as a white fluffy solid.

Example 2

N-Carbonyl-Phentermine—BSA Immunogen

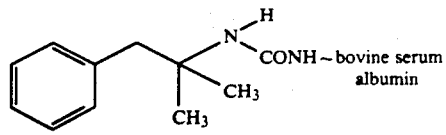

Phentermine hydrochloride (100 mg, 0.54 mmol), dissolved in anhydrous acetonitrile (5.0 ml), was added dropwise over 15 minutes to a stirred solution of disuccinimidyl carbonate (276 mg, 1.08 mmol) dissolved in ten milliliters of the same solvent. After stirring for three hours at room temperature, the solvent was removed in vacuo, and the residue was taken up in chloroform. The residue was washed twice with 20-milliliter portions of water, 1N HCl, water, saturated sodium bicarbonate solution and brine. After drying the organic extracts over magnesium sulfate, the solvent was evaporated to yield 110 milligrams of phentermine-N-hydroxy succinimide urethane.

Phentermine-N-hydroxy succinimide urethane (20 mg, 0.07 mmol), dissolved in a 1:1 solution of dimethylformamide and tetrahydrofuran (400 µl), was added to bovine serum albumin (119 mg) dissolved in phosphate buffer (10 ml) at pH 8.2. After stirring overnight at room temperature, the solution was dialyzed extensively against the phosphate buffer and then distilled water. Lyophilization of the protein solution yielded 110 milligrams of the immunogen as a white fluffy solid.

Example 3

Alpha-Methyl-d,l-Phenylalanine—BSA Immunogen

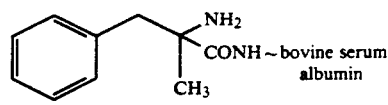

Trifluoroacetic anhydride (1.0 ml, 7.08 mmol) was added dropwise to a stirred suspension of alpha-methyl-d,l-phenylalanine (100 mg, 0.56 mmol) in pyridine at 0° C. The solids gradually dissolved, and the solution turned pale yellow. After 20 minutes of additional stirring, the cooling bath was removed and stirring was continued for an additional one hour. The solution was then poured over ice, acidified with 2N HCl (10 ml) and extracted with two 15-milliliter portions of ethyl acetate. The combined organic extracts were washed with brine and dried over sodium sulfate. Evaporation in vacuo yielded 150 milligrams of N-trifluoroacetyl-alpha-methyl-d,l-phenylalanine.

Dicyclohexylcarbodiimide (19 mg, 0.092 mmol), N-hydroxy succinimide (11 mg, 0.092 mmol) and N-trifluoroacetyl-alpha-methyl-d,l-phenylalanine (23 mg, 0.083 mmol) were dissolved in anhydrous dimethylformamide (500 µl). The reaction mixture was stirred for three hours at room temperature. The cloudy suspension was filtered and then added dropwise to a stirred solution of BSA (141 mg) dissolved in 0.1N phosphate buffer (3.6 ml, pH 8). After stirring at room temperature for 18 hours, the suspension was dialyzed extensively against distilled water and lyophilized to yield 135 milligrams of a white fluffy powder. The N-trifluoroacetyl protecting group was removed by dissolving the protein in a solution of methanol (9.0 ml), piperidine (3.0 ml) and saturated aqueous sodium bicarbonate (1.0 ml). The volume was adjusted to 30 milliliters with water. After standing at room temperature for six hours, the solution was dialyzed extensively against distilled water and lyophilized to yield 104 milligrams of the immunogen as a white fluffy powder.

Example 4

N-Carboxymethyl-Phenylpropanolamine~BSA Immunogen

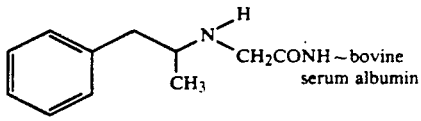

Phenylpropanolamine (6.78 g, 44.9 mmol) was dissolved in chloroform (40 ml) and set to reflux. Ethyl bromoacetate (5.97 g, 53.8 mmol) was added dropwise, and the resulting suspension was refluxed for an additional 30 minutes. Triethylamine (6.87 ml, 49.3 mmol) was added to dissolve the salt of the product. After a total of seven hours of heating, the solvent was removed in vacuo leaving an oily crystalline residue. The residue was partitioned between ethyl acetate (50 ml) and an HCl solution (20 ml, at pH 1). The aqueous layer was drawn off, adjusted to pH 7 with 1N NaOH and extracted with three 20-milliliter portions of chloroform. After drying the organic extracts over sodium sulfate, the solvents were removed to yield 7.19 grams of N-carboethoxymethyl-phenylpropanolamine as a colorless oil.

N-Carboethoxymethyl-Phenylpropanolamine (2.57 g, 10.8 mmol) and di-tert-butyl dicarbonate (2.01 g, 13.0 mmol) were dissolved in anhydrous tetrahydrofurane (20 ml). Triethylamine (2.73 ml, 19.6 mmol) and 4-N,N-dimethylamino pyridine (20 mg) were then added. After stirring for three hours at room temperature, an additional 500 microliters of di-tert-butyl dicarbonate (3.2 mmol) were added and stirring was continued for one hour more. The solution was concentrated in vacuo, dissolved in ethyl acetate (30 ml), washed with four 20-milliliter portions of water and dried over sodium sulfate. Removal of the solvent yielded 4.1 grams of crude product. The product was chromatographed on a silica gel column to yield 3.3 grams of a diastereomeric mixture of N-tert-butoxycarbonyl-N-carboethoxymethyl-phenylpropanolamine.

N-Tert-Butoxycarbonyl-N-Carboethoxymethyl-Phenylpropanolamine (1.78 g, 5.30 mmol) was dissolved in a solution composed of tetrahydrofuran (20 ml), methanol (20 ml), and 10% aqueous sodium hydroxide (20 ml). Stirring was continued for three hours, whereupon the pale yellow solution was diluted with water (50 ml) and extracted with three 30-milliliter portions of chloroform. The aqueous solution was adjusted to pH 4 with 2N HCl and then extracted with three 20-milliliter portions of chloroform. The combined organic extracts were dried over sodium sulfate and evaporated in vacuo to yield 0.96 grams of N-tert-butoxycarbonyl-N-carboxymethyl-phenylpropanolamine as a white foam.

Seventy-three milligrams of N-tert-butoxycarbonyl-N-carboxymethyl-phenylpropanolamine (0.24 mmol), dicyclohexylcarbodiimide (97 mg, 0.47 mmol) and N-hydroxysuccinimide (54 mg, 0.47 mmol) were dissolved and stirred in anhydrous dimethylformamide (1.5 ml) at room temperature for three hours. The resultant suspension was filtered and added dropwise to a stirred solution of BSA (401 mg) dissolved in 0.1M phosphate buffer (7.2 ml, at pH 8). After stirring overnight, the solution was diluted with water (10 ml) and dialyzed extensively against distilled water. Lyophilization yielded 395 milligrams of a white fluffy powder. The t-BOC protecting group was removed by dissolving the protein in 50 milliliters of a 1:1 solution of methylene chloride/trifluoroacetic acid. After stirring the clear solution at room temperature for five minutes, the solvent was removed in vacuo, and the oily residue was dissolved in a 4% aqueous solution of sodium bicarbonate (30 ml). The basic solution was dialyzed extensively against distilled water and lyophillized to yield 357 milligrams of N-carboxymethyl-phenylpropanolamine immunogen.

Example 5

N-Methyl-d,l-Phenylalanine~BSA Immunogen

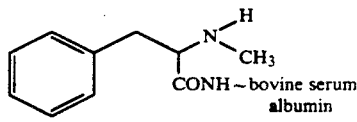

N-BOC-N-Methyl-d,l-Phenylalanine (49 mg, 0.176 mmol) was dissolved in dimethylformamide (0.50 ml). N,N'-Disuccinimidyl Carbonate (54 mg., 0.211 mmol) was added to the solution, and the reaction mixture was stirred under nitrogen for two hours. The reaction mixture was then added dropwise to a solution of BSA (300 mg, 0.0044 mmol) dissolved in phosphate buffer (6.3 ml, 0.1M, pH 7.5) and 1,4-dioxane (2.3 ml). After stirring for six hours, the reaction mixture was dialyzed against distilled water and then lyophilized. Product yield was 258 milligrams of N-BOC-N-methyl-d,l-phenylalanine~BSA.

N-BOC-N-Methyl-d,l-Phenylalanine~BSA (230 mg) was partially dissolved in methylene chloride (15 ml). Trifluoroacetic acid (15 ml) was added, and the reaction mixture was stirred for five minutes. Solvent was removed in vacuo, the residue was redissolved in phosphate buffer (40 ml, 0.1M, pH 7.5), and the reaction mixture was dialyzed extensively against distilled water. Product yield after lyophilization was 182 milligrams of immunogen.

Example 6 d,l-Phenylalanine~BSA Immunogen

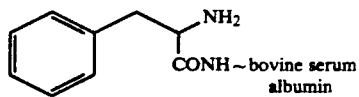

N-BOC-l-Phenylalanine (23.5 mg, 0.0886 mmol) and N-BOC-d-phenylalanine (23.5 mg, 0.0886 mmol) were combined in dimethylformamide (0.50 ml) and coupled to BSA (300 mg, 0.0044 mmol) substantially in accordance with the procedure described previously in Example 5 (N-methyl-d,l-phenylalanine~BSA). Product yield was 198 milligrams of N-BOC-d,l-phenylalanine~BSA.

N-BOC-d,l-Phenylalanine~BSA (170 mg) was reacted with trifluoroacetic acid/methylene chloride substantially in accordance with the procedure previously described in Example 5 (N-methyl-d,l-phenylalanine~BSA). Product yield was 135 milligrams of immunogen.

Example 7

1-Carboxymethoxy-Phentermine~BSA Immunogen

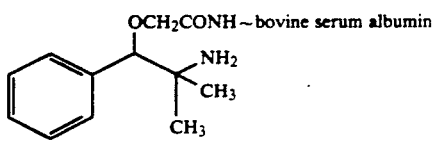

Two grams of 2-amino-2-methyl-1-propanol (22.4 mmol) was dissolved in dimethylformamide (20 ml). Triethylamine (5.6 ml, 40.3 mmol) and di-tertbutyldicarbonate (5.38 g, 24.7 mmol) were added, and the reaction mixture was stirred under nitrogen for 16 hours. Solvent was removed in vacuo, and the crude product purified on a silica gel column eluted with ethyl acetate. Product yield was 3.98 grams.

The resulting N-BOC-2-amino-2-methyl-1-propanol (3.69 g, 19.5 mmol) was dissolved in methylene chloride (74 ml) and added to a stirred suspension of Dess-Martin periodinane (10.75 g, 25.35 mmol; Aldrich Chemical Company, Milwaukee, WI) in methylene chloride (89 ml). After stirring for 20 minutes under nitrogen, the reaction mixture was diluted with diethyl ether (370 ml), poured into sodium hydroxide (148 ml, 1.3M) and stirred for ten minutes. The aqueous sodium hydroxide layer was separated and discarded. The remaining organic solution was washed successively with sodium hydroxide (148 ml, 1.3M) and H$_2$O (185 ml). After drying over magnesium sulfate, the solvent was removed in vacuo to yield 3.21 grams of N-BOC-2-methyl-1-propanal.

One gram of N-BOC-2-amino-2-methyl-1-propanal (5.34 mmol) was dissolved in freshly distilled tetrahydrofuran (10 ml) and cooled to $-78°$ C. Phenyllithium (6.5 ml, 11.75 mmol) was added, and the solution was stirred at $-78°$ C. for ten minutes. The pH was then adjusted to 4 with acetic acid. The reaction mixture was poured into ice water (200 ml) and quickly extracted with diethyl ether (200 ml). The organic extract was washed with H$_2$O (2×200 ml) and dried over magnesium sulfate. The solvent was then removed in vacuo. Crude product was purified on a silica gel column eluted with ethyl acetate/hexane (20/80). Product yield was 956 milligrams of N-BOC-1-hydroxy-phentermine.

Sodium hydride (288 mg, 60%, 7.20 mmol) was washed with hexane, stirred-suspended in dimethylformamide (4.5 ml) and cooled to 0° C. N-BOC-1-Hydroxy-Phentermine (919 mg, 3.46 mmol) was dissolved in dimethylformamide (2.0 ml) and added to the sodium hydride suspension, and the reaction mixture was stirred under nitrogen, at 0° C. for 20 minutes. At that time, ethyl bromoacetate (0.479 ml, 4.32 mmol) was added, and the reaction mixture was stirred for 45 minutes at 0° C. under nitrogen. The reaction solution was then diluted with ethyl acetate (50 ml), adjusted to pH 5 with acetic acid and filtered. Filtrate solvent was removed in vacuo, and the crude product purified on a silica gel column eluted with ethyl acetate/hexane (20/80). Product yield was 145 milligrams of N-BOC-1-carboethoxymethoxy-phentermine.

One hundred and forty-five milligrams of N-BOC-1-carboethoxymethoxy-phentermine (0.413 mmol) was dissolved in methanol (1.5 ml), cooled to 0° C., and sodium hydroxide (0.825 ml, 1M, 0.825 mmol) was added. After stirring for 40 minutes at 0° C., the pH was adjusted to 5 with 0.1M hydrochloric acid, and the solvent was removed in vacuo. The resulting white solid was triturated with ethyl acetate (10.0 ml) and filtered. The filtrate solvent was removed in vacuo to yield 110 milligrams of N-BOC-1-carboxymethoxy-phentermine.

N-BOC-1-Carboxymethoxy-Phentermine (62.0 mg, 0.192 mmol) was dissolved in dimethylformamide (0.50 ml). N-Hydroxysuccinimide (26 mg, 0.230 mmol) and 1,3-dicyclohexylcarbodiimide (47 mg, 0.230 mmol) were added, and the reaction mixture was stirred under nitrogen for 17 hours. The reaction mixture was then filtered and added dropwise to a solution of BSA (326 mg, 0.0048 mmol) dissolved in 0.1M phosphate buffer (5.4 ml, pH 7.6) and p-dioxane (3.6 ml). After six hours of stirring, the reaction mixture was dialyzed extensively against distilled water and lyophilized to yield 166 milligrams of N-BOC-1-carboxymethoxy-phentermine~BSA.

N-BOC-1-Carboxymethoxy-Phentermine~BSA (80 mg) was reacted with trifluoroacetic acid/methylene chloride substantially in accordance with the procedure previously described in Example 5 (N-methyl-d,l-phenylalanine~BSA). Product yield was 76 milligrams of immunogen.

SYNTHESIS OF TRACERS

Example 8

N-Acetamidomethylfluorescein-d,l-Amphetamine Tracer

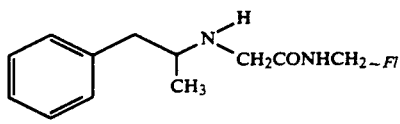

Thirty milligrams of N-BOC-N-acetic acid-d,l-amphetamine (0.102 mmol) was dissolved in dimethylformamide (0.400 ml). Fourteen milligrams of N-hydroxysuccinimide (0.123 mmol) was added, followed by 1,3-dicyclohexylcarbodiimide (25 mg, 0.123 mmol), and the reaction solution was stirred under nitrogen for 16 hours. The solution was then filtered into a flask containing aminomethylfluorescein hydrochloride (41 mg, 0.102 mmol, pH adjusted to 9 with triethylamine), and the solution was stirred under nitrogen for one hour. Solvent was removed in vacuo, and the crude product was purified on two 1.0 millimeter C18 reverse-phase preparative thin layer chromatography plates eluted with H$_2$O/methanol/acetic acid (30/70/0.4). The purified product yield was 34 milligrams of N-BOC-N-acetamidomethylfluorescein-d,l-amphetamine.

Thirty-four milligrams of N-BOC-N-acetamidomethylfluorescein-d,l-amphetamine (0.0534 mmol) was dissolved in methylene chloride (0.50 ml). Trifluoroacetic acid (0.50 ml) was added, and after stirring for five minutes solvent was removed in vacuo. The residue was redissolved in methylene chloride (about 10 ml) and pH adjusted to 9 with triethylamine. Solvent was again removed in vacuo, and the crude product was purified on a 1.0 millimeter C18 reverse-phase preparative thin layer chromatography plate eluted with H2O/methanol/acetic acid (30/70/0.4). The purified product yield was 26 milligrams of N-acetamidomethylfluorescein-d,l-amphetamine tracer.

Example 9

5- and 6-Carboxyfluorescein Phenterminamide Tracer

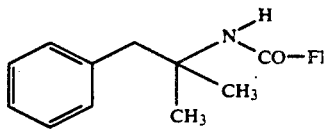

Phentermine hydrochloride (50 mg, 0.27 mmol) was dissolved in dimethylformamide (1.0 ml). Triethylamine (27 mg) was added to the solution, at room temperature while stirring, followed by the addition of 5(6)-carboxyfluorescein-N-hydroxysuccinimide ester (127 mg, 0.27 mmol). The orange solution was stirred at room temperature in the dark for 18 hours. The solvent was evaporated in vacuo, and the tracer isolated by preparative thin layer chromatography.

Example 10

Aminomethylfluorescein-Phentermine Urea Tracer

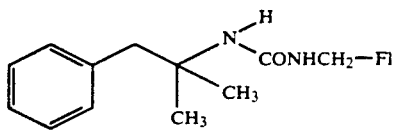

Phentermine-N-Hydroxy Succinimide Urethane was prepared substantially in accordance with the procedure described in Example 2. Phentermine-N-Hydroxy Succinimide Urethane (50 mg, 0.17 mmol) and aminomethyl fluorescein hydrochloride (69 mg, 0.19 mmol) were dissolved in anhydrous dimethylformamide (1.0 ml, containing triethylamine 17 mg). After stirring for two hours at room temperature, the tracer product was isolated by reverse-phase preparative thin layer chromatography using water/methanol (8/2) as eluant. The yield of aminomethyl fluorescein-phentermine urea tracer was 28 milligrams.

Example 11

N-(2-Aminopropyl)-d,l-Amphetamine 5- and 6-Carboxyfluoresceinamide Tracers

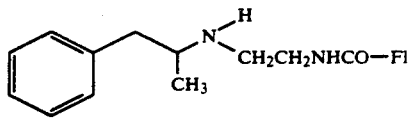

2-Bromo-1-Phenylpropane (1.11 g, 5.58 mmol) and ethylene diamine (9.55 g, 159 mmol) were combined and refluxed for 18 hours. The excess ethylene diamine was removed under high vacuum, and the resulting residue was partitioned between 50 milliliters of 0.1N NaOH and 100 milliliters of benzene. The organic phase was washed with three 50-milliliter portions of water, and the benzene layer was dried over magnesium sulfate and evaporated to yield 0.50 grams of N-(2-aminoethyl)-d,l-amphetamine as a colorless oil.

N-(2-Aminopropyl)-d,l-Amphetamine (27 mg, 0.15 mmol) and a 1:1 mixture of 5- and 6-carboxyfluorescein N-hydroxysuccinimide esters (72 mg, 0.15 mmol) were combined in dimethylformamide (1.0 ml, containing triethylamine 21 µl). After stirring for 18 hours at room temperature, the solvents were removed in vacuo, and the tracers were isolated by reverse-phase preparative thin layer chromatography using methanol/water/trifluoroacetic acid (40/59/1) as eluant.

Example 12

N-(3-Aminopropyl)-d,l-Amphetamine 5-Carboxyfluoresceinamide Tracer

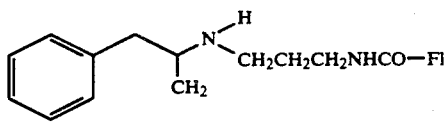

2-Bromo-1-Phenylpropane (1.24 g, 6.23 mmol) and propylene diamine (15.0 ml, 180 mmol) were combined in absolute ethanol (120 ml) and were set to reflux for 18 hours. The excess ethylene diamine was removed under high vacuum, and the resulting residue was filtered to remove insoluble salts and was partitioned between 10 milliliters of 4N NaOH and 50 milliliters of benzene. The organic phase was washed with two five-milliliter portions of water, and the benzene layer was dried over magnesium sulfate and evaporated to yield N-(3-aminopropyl)-d,l-amphetamine as a colories oil.

Thirty-five milligrams of N-(3-aminopropyl)-d,l-amphetamine (0.12 mmol) and 5-carboxyfluorescein N-hydroxysuccinimide ester (55 mg, 0.12 mmol) were dissolved in anhydrous dimethylformamide (600 µl). After stirring for 18 hours at room temperature, the solvent was removed under high vacuum, and the tracer was isolated by reverse-phase preparative thin layer chromatography using methanol/water (80/20) as eluant.

EXAMPLE 13

N-Methyl-d,l-Phenylalanine-Ethylenediamine-5-Carboxyfluoresceinamide Tracer

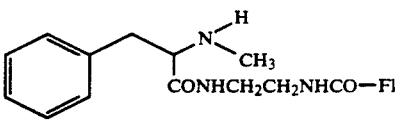

N-Methyl-l-Phenylalanine (100 mg, 1.68 mmol) and N-methyl-d-phenylalanine (300 mg, 1.68 mmol) were combined in dimethylformamide (6.0 ml). Triethylamine (0.84 ml, 6.04 mmol) and di-tert-butyl dicarbonate (0.846 ml, 3.69 mmol) were added, and the reaction mixture was stirred under nitrogen for 18 hours. The reaction mixture was then filtered, and the solvent was removed in vacuo to give N-BOC-N-methyl-d,l-phenylalanine (1.1 g) as a pale yellow oil (some dimethylformamide was still present).

Fifty milligrams of the resulting N-BOC-N-methyl-d,l-phenylalanine (0.179 mmol) was dissolved in dimethylformamide (0.50 ml). N,N'-Disuccinimidyl Carbonate (55 mg, 215 mmol) was added, and the reaction mixture was stirred under nitrogen for two hours. A small aliquot (0.156 ml, 0.056 mmol) of the reaction mixture was then added to a solution of N-5-carboxyfluorescein-ethylenediamine (24 mg, 0.056 mmol) dissolved in dimethylformamide (0.50 ml). The pH was adjusted to 9 with triethylamine, and the reaction was stirred for 30 minutes under nitrogen. Solvent was then removed in vacuo, and the product was isolated on a 1.0 millimeter silica gel preparative thin layer chromatography plate eluted with ethyl acetate/methanol (80/20). Product yield was 19 milligrams of N-BOC-N-methyl-d,l-phenylalanine-ethylenediamine-5-carboxyfluorescein.

Nineteen milligrams of the product (0.028 mmol) was reacted with trifluoroacetic acid/methylene chloride, substantially in accordance with the procedure previously described in Example 8 (N-acetamidomethylfluorescein-d,l-amphetamine tracer). Product yield was 14 milligrams of tracer.

EXAMPLE 14

N-Methyl-d,l-Phenylalanine-Aminomethylfluorescein Tracer

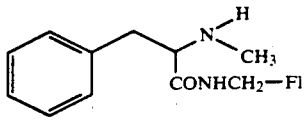

Fifty milligrams of N-BOC-N-methyl-d,l-phenylalanine (0.179 mmol) were dissolved in dimethylformamide (0.50 ml). N,N'-Disuccinimidyl Carbonate (55 mg, 0.215 mmol) was added, and the reaction mixture was stirred under nitrogen for two hours. A small aliquot (0.300 ml, 0.108 mmol) of the reaction mixture was then added to a solution of aminomethylfluorescein hydrochloride (35 mg, 0.088 mmol) dissolved in dimethylformamide (0.20 ml). The pH was adjusted to 9 with triethylamine, and the reaction mixture was stirred for 60 minutes under nitrogen. Solvent was then removed in vacuo, and the product isolated on a 1.0 millimeter silica gel preparative thin layer chromatography plate eluted with ethyl acetate/methanol (80/20). Product yield was 27 milligrams of N-BOC-N-methyl-d,l-phenylalanine-aminomethylfluorescein.

N-BOC-N-Methyl-d,l-Phenylalanine-Aminomethylfluorescein (23 mg, 0.037 mmol) was reacted with trifluoroacetic acid/methylene chloride substantially in accordance with the procedure previously described in Example 8 (N-acetamidomethylfluorescein-d,l-amphetamine tracer). Product yield was 14 milligrams of tracer.

EXAMPLE 15 d,l-Phenylalanine-Aminomethylfluorescein Tracer

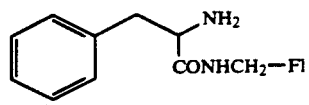

N-BOC-d-Phenylalanine (10 mg, 0.0375 mmol) and N-BOC-l-phenylalanine (10 mg. 0.0375 mmol) were combined in dimethylformamide (0.20 ml). Nineteen milligrams of 2-ethyl-5-phenylisoxazolium-3'-sulfonate (0.075 mmol), were added, followed by the addition of triethylamine (0.010 ml, 0.075 mmol), and the reaction mixture was stirred for 30 minutes under nitrogen. The reaction mixture was then added to a solution of aminomethylfluorescein hydrochloride (10 mg, 0.025 mmol) and triethylamine (0.005 ml, 0.036 mmol) dissolved in dimethylformamide (0.20 ml). After 18 hours of stiring under nitrogen, the solvent was removed in vacuo, and the product was isolated on a 1.0 millimeter C18 reverse-phase preparative thin layer chromatography plate eluted with H$_2$O/methanol/acetic acid (30/70/0.4). Product yield was 9.5 milligrams of N-BOC-d,l-phenylalanine-aminomethylfluorescein.

The product (9.5 mg, 0.0156 mmol) was reacted with trifluoroacetic acid/methylene chloride, substantially in accordance with the procedure described previously in Example 8 (N-acetamidomethylfluorescein-d,l amphetamine tracer). Product yield was 6.0 milligrams of tracer.

EXAMPLE 16

N-Carboxyethyl-Amphetamine-Aminomethylfluorescein Tracer

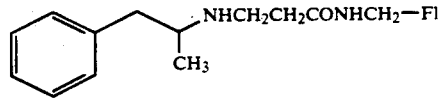

Phenylacetone (100 mg, 0.745 mmol) was dissolved in anhydrous methanol (2.0 ml). Beta-alanine (398 mg, 4.47 mmol) was added, followed by sodium cyanoborohydride (94 mg, 1.49 mmol). After 18 hours of stirring under nitrogen, the reaction mixture was filtered, and the filtrate solvent was removed in vacuo. The resulting crude material was purified on four 1.0 millimeter C18 reverse-phase preparative thin layer chromatography plates eluted with H$_2$O/methanol/acetic acid (40/60/0.4). The material obtained was dissolved in ethyl acetate (20 ml) and was extracted with 1.0M sodium bicarbonate (3×20 ml). The aqueous extracts were combined, the pH was adjusted to 4 with 1.0M hydrochloric acid, and the solvent was removed in vacuo. The resulting crystalline solid was then triturated twice with 50-milliliter portions of ethyl acetate and filtered. The filtrates were combined, and the solvent was removed in vacuo to yield 93 milligrams of N-carboxyethyl-amphetamine.

N-Carboxyethyl-Amphetamine (93 mg, 0.449 mmol) was dissolved in dimethylformamide (1.0 ml). Triethylamine (0.113 ml, 0.808 mmol) was added, followed by di-tert-butyl-dicarbonate (108 mg, 0.493 mmol). After stirring under nitrogen for three hours, the solvent was removed in vacuo, and the crude product are purified on two 1.0 millimeter C18 reverse-phase preparative thin layer chromatography plates eluted with H$_2$O/methanol/acetic acid (30/70/0.4). Product yield was 33 milligrams of N-BOC-N-carboxyethyl-amphetamine.

Thirty-three milligrams of N-BOC-N-carboxyethyl-amphetamine (0.107 mmol) were dissolved in dimethylformamide (0.80 ml). N-Hydroxysuccinimide (15 mg, 0.129 mmol) was added, followed by 1,3-dicyclohexylcarbodiimide (27 mg, 0.129 mmol). After stirring for 19 hours under nitrogen, the reaction mixture was filtered into a flask containing aminomethylfluorescein hydrochloride (43 mg, 0.107 mmol). The pH was adjusted to 9 with triethylamine, and the solution was stirred for 24 hours under nitrogen, in the dark. The solvent was removed in vacuo, and the crude product was purified on two 1.0 millimeter C18 reverse-phase preparative thin layer chromatography plates eluted with H₂O/methanol/acetic acid (30/70/0.4). Product yield was 26 milligrams of N-BOC-N-carboxyethyl-amphetamine-aminomethylfluorescein.

Twenty milligrams of N-BOC-N-carboxyethyl-amphetamine-aminomethylfluorescein (0.031 mmol) were reacted with trifluoroacetic acid/methylene chloride substantially in accordance with the procedure described previously in Example 8 (N-acetamidomethylfluorescein-d,l-amphetamine tracer). Product yield was 14 milligrams of tracer.

Example 17

N-Carboxymethyl-Amphetamine-Ethylaminomethylfluorescein Tracer

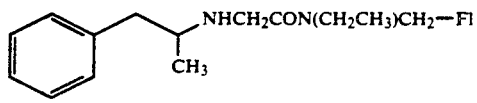

Twenty-one milligrams of N-BOC-N-carboxymethyl-amphetamine (0.0716 mmol) were coupled to N-ethyl-aminomethylfluorescein (33 mg, 0.0716 mmol) substantially in accordance with the procedure previously described in Example 16 (N-BOC-N-carboxyethyl-amphetamine-aminomethylfluorescein tracer). Product yield was 31 milligrams of N-BOC-N-carboxymethyl-amphetamine-ethylaminomethylfluorescein.

Twenty-one milligrams of N-BOC-N-carboxymethyl-amphetamine-ethylaminomethylfluorescein (0.030 mmol) were reacted with trifluoroacetic acid/methylene chloride substantially in accordance with the procedure previously described in Example 8 (N-acetamidomethylfluorescein-d,l-amphetamine tracer). Product yield was 15 milligrams of tracer.

Example 18

N-Carboxymethyl-Amphetamine-Butylaminomethylfluorescein Tracer

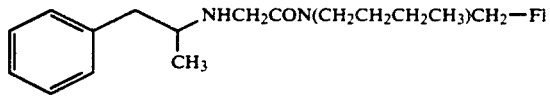

Sixteen milligrams of N-BOC-N-carboxymethyl-amphetamine (0.0545 mmol) were coupled to N-butyl-aminomethylfluorescein (27 mg, 0.0545 mmol) substantially in accordance with the procedure previously described in Example 15 (N-BOC-d,l-phenylalanine-aminomethylfluorescein tracer). Product yield was 28 milligrams of N-BOC-N-carboxymethyl-amphetamine-butylaminomethylfluorescein.

Twenty milligrams of N-BOC-N-carboxymethyl-amphetamine-butylaminomethylfluorescein (0.029 mmol) were reacted with trifluoroacetic acid/methylene chloride substantially in accordance with the procedure previously described in Example 8 (N-acetamidomethylfluorescein-d,l-amphetamine tracer). Product yield was 12 milligrams of tracer.

AMPHETAMINE-CLASS FLUORESCENCE POLARIZATION IMMUNOASSAYS

As described previously, the reagents of the FPIA of the present invention comprise tracers and antibodies specific for the amphetamine-class analytes. In addition, conventionally used assay solutions including a dilution buffer, and d,l-amphetamine calibrators and d,l-amphetamine controls are prepared. Typical solutions of these reagents are commercially available in assay "kits" from Abbott Laboratories, Abbott Park, Ill.

The preferred assay procedure was designed to be conducted on a TDx®, IMx® or ADx™ Systems, which are available from Abbott Laboratories, Abbott Park, Ill. When such an instrument is used, the assay is fully automated from pretreatment to final reading. Manual assays, however, can also be performed. In either case, the test sample can be mixed with a pretreatment solution in dilution buffer before a background reading is taken. The tracer is then added to the test solution, followed by the addition of the antibody. After incubation, a fluorescence polarization reading is taken.

In the automated assays, the fluorescence polarization value of each calibrator, control or test sample is determined and printed on the output tape of the instrument. The instrument also generates a standard curve by plotting the polarization of each calibrator versus its concentration, using a nonlinear regression analysis. The concentration of each control or sample is read from the calibration curve and printed on an output tape.

Example 19

Elimination of Riboflavin Fluorescence Interference

Fluorescence interference by riboflavin may render the assay results inaccurate. Therefore, it is advantageous to eliminate riboflavin's potential for interference by adding a riboflavin binding protein to the test sample. The benefits of pretreating samples with a riboflavin binding protein are illustrated in Table 1 below: the second and third columns represent fluorescence intensity measurements which were obtained before tracer was added to untreated and pretreated (5 mg/ml of riboflavin binding protein) drug-free urine samples, and the fourth and fifth columns represent polarization measurements after the tracer was added to untreated and pretreated drug-free urine samples. The pretreatment solution comprised 0.1M Tris buffer (pH 7.5), 0.01% bovine gamma globulin, 0.1% sodium azide and 5 mg/ml of riboflavin binding protein.

TABLE 1

Test Sample Pretreatment Using Riboflavin Binding Protein

| Sample Number | Background Intensity* untreated sample before tracer | Background Intensity* pretreated sample before tracer | Polarization** untreated sample after tracer | Polarization** pretreated sample after tracer |
|---|---|---|---|---|
| 2 | 6074 | 348 | 252.27 | 248.48 |
| 3 | 19058 | 979 | 257.85 | 246.47 |
| 4 | 7952 | 415 | 258.32 | 247.59 |
| 5 | 4505 | 241 | 252.41 | 247.79 |
| 7 | 30526 | 1212 | 267.66 | 247.39 |
| 8 | 24964 | 1049 | 259.42 | 247.91 |
| 9 | 22649 | 953 | 259.98 | 244.59 |
| 10 | 12296 | 450 | 254.08 | 246.92 |
| 11 | 24292 | 1459 | 260.36 | 249.19 |
| 12 | 13157 | 582 | 252.77 | 246.78 |
| 13 | 9112 | 477 | 249.26 | 247.29 |
| 14 | 23622 | 890 | 253.47 | 245.90 |
| 15 | 4269 | 854 | 251.15 | 248.60 |
| 16 | 4985 | 393 | 250.08 | 246.88 |
| 17 | 4217 | 473 | 250.43 | 247.51 |

*in fluorescence intensity units
**in millipolarization units

A comparison of the second and third columns of Table 1 illustrates that the pretreatment of a test sample with the riboflavin binding protein decreases the background intensity of the test sample. A comparison of the fourth and fifth columns illustrates that such pretreatment of a test sample prior to the assay acts to decrease the fluorescence interference by riboflavin.

Example 20

FPIA Specificity

The assay system of the present invention is desirable for the detection of amphetamine-class drugs such as amphetamine, methamphetamine, phenylpropanolamine, ephedrine, pseudoephedrine and phentermine. The cross-reactivity of a variety of amphetamine-class drugs were tested. Compounds were assayed by adding a known quantity of the test compound to drug-free normal human urine and assaying with the amphetamine-class assay on the TDx ® instrument. The percent cross-reactivity equals 100×(concentration of test compound found/concentration of test compound added). The results obtained are shown in Table 2 below. The data demonstrate that the assay system and reagents of the present invention have sufficient cross-reactivity to detect amphetamine-class drugs at concentrations which produce a stimulating or toxic effect. At the same time, concentrations of phenethylamine-like substances which are common in certain foods, e.g.s, tryptamine and tyramine, are not readily detected and therefore do not present interference problems.

TABLE 2

| Test Compound | FPIA Specificity | | |
|---|---|---|---|
| | Concentration Added (μg/ml) | Concentration Found (μg/ml) | % Cross-Reactivity |
| d-Amphetamine | 100 | HIGH | — |
| | 10 | 5.11 | 51.10 |
| | 1 | 0.78 | 78.00 |
| | 0.5 | 0.37 | 74.00 |
| l-Amphetamine | 100 | HIGH | — |
| | 10 | 5.09 | 50.90 |
| | 1 | 0.40 | 40.00 |
| | 0.5 | 0.22 | 44.00 |
| N-Ethyl-3,4-Methylene-Dioxyamphetamine | 100 | 3.97 | 3.97 |
| | 10 | 0.78 | 7.80 |
| | 5 | 0.55 | 11.00 |
| | 1 | 0.21 | 21.00 |
| 3,4-Methylene-Dioxyamphetamine | 100 | 1.95 | 1.95 |
| | 50 | 1.14 | 2.28 |
| | 5 | 0.32 | 6.40 |
| 3,4-Methylene-Dioxymethamphetamine | 100 | 3.08 | 3.08 |
| | 50 | 1.99 | 3.98 |
| | 5 | 0.52 | 10.40 |
| | 1 | 0.28 | 28.00 |
| d-Methamphetamine | 100 | HIGH | — |
| | 10 | 5.60 | 56.00 |
| | 1 | 1.37 | 137.00 |
| | 0.5 | 0.88 | 176.00 |
| l-Methamphetamine | 100 | HIGH | — |
| | 10 | HIGH | — |
| | 1 | 0.85 | 85.00 |
| | 0.5 | 0.46 | 92.00 |
| d,l-Methamphetamine | 100 | HIGH | — |
| | 10 | HIGH | — |
| | 1 | 1.98 | 198.00 |
| | 0.5 | 1.04 | 208.00 |
| Benzphetamine | 100 | HIGH | — |
| | 10 | 1.83 | 18.30 |
| | 5 | 1.03 | 20.60 |
| | 1 | 0.24 | 24.00 |
| Chlorphentermine | 100 | HIGH | — |
| | 10 | 1.34 | 13.40 |
| | 5 | 0.82 | 16.40 |

TABLE 2-continued

| Test Compound | FPIA Specificity | | |
|---|---|---|---|
| | Concentration Added (μg/ml) | Concentration Found (μg/ml) | % Cross-Reactivity |
| | 1 | 0.20 | 20.00 |
| Diethylpropion | 500 | 1.10 | 0.22 |
| | 100 | 0.39 | 0.39 |
| l-Ephedrine | 100 | 4.20 | 4.21 |
| | 10 | 1.35 | 13.50 |
| | 5 | 0.93 | 18.60 |
| | 1 | 0.39 | 39.00 |
| d,l-Ephedrine | 100 | HIGH | — |
| | 10 | 3.00 | 30.00 |
| | 1 | 0.66 | 66.00 |
| | 0.5 | 0.34 | 68.00 |
| d-Pseudoephedrine | 100 | 3.02 | 3.02 |
| | 50 | 1.68 | 3.36 |
| | 20 | 0.84 | 4.20 |
| | 10 | 0.34 | 3.40 |
| l-Pseudoephedrine | 100 | HIGH | — |
| | 10 | 0.96 | 9.60 |
| | 5 | 0.50 | 10.00 |
| | 1 | 0.12 | 12.00 |
| Fenfluramine | 100 | 3.98 | 3.98 |
| | 10 | 0.64 | 6.40 |
| | 5 | 0.39 | 7.80 |
| Isometheptene | 100 | HIGH | — |
| | 10 | 0.84 | 8.40 |
| | 5 | 0.44 | 8.80 |
| Isoxsuprine | 100 | 4.00 | 4.00 |
| | 10 | 0.61 | 6.10 |
| Mephentermine | 100 | HIGH | — |
| | 10 | 1.74 | 17.40 |
| | 5 | 0.98 | 19.60 |
| Methylphenidate | 500 | 0.43 | 0.09 |
| | 100 | 0.10 | 0.10 |
| Nylidrin | 100 | HIGH | — |
| | 10 | 1.18 | 11.80 |
| | 5 | 0.69 | 13.80 |
| Phendimetrazine | 500 | 2.05 | 0.41 |
| | 100 | 0.59 | 0.59 |
| Phenmetrazine | 100 | 3.63 | 3.63 |
| | 10 | 0.82 | 8.20 |
| | 5 | 0.52 | 10.40 |
| | 1 | 0.15 | 15.00 |
| Phentermine | 100 | HIGH | — |
| | 10 | 1.95 | 19.50 |
| | 5 | 1.02 | 20.40 |
| Phenylpropanolamine | 100 | HIGH | — |
| | 10 | 1.09 | 10.90 |
| | 5 | 0.62 | 12.40 |
| Propylhexedrine | 100 | HIGH | — |
| | 10 | 5.13 | 51.30 |
| | 5 | 2.75 | 55.00 |
| | 1 | 0.93 | 93.00 |
| | 0.5 | 0.48 | 96.00 |
| Phenethylamine | 100 | HIGH | — |
| | 20 | 1.10 | 5.50 |
| | 10 | 0.52 | 5.20 |
| Tranylcypromine | 100 | HIGH | — |
| | 10 | 1.97 | 19.70 |
| | 5 | 1.07 | 21.40 |
| | 1 | 0.22 | 22.00 |
| Tryptamine | 1000 | 2.62 | 0.26 |
| | 100 | 0.20 | 0.20 |
| Tyramine | 1000 | 0.64 | 0.06 |
| | 100 | not detected | — |

The following reagents were used in the preferred automated amphetamine-class drugs assay:
1) the pretreatment solution, described above, containing the riboflavin binding protein;
2) the tracer (0.36 μg/ml, prepared as described above in Example 8) in 0.1M Tris buffer (pH 7.5) containing 0.01% bovine gamma globulin and 0.1% sodium azide;

3) the antibody, comprising sheep antiserum raised against an amphetamine-immunogen (prepared as described above in Example 1) and diluted in 0.1M Tris buffer (pH 7.5) containing 0.01% bovine gamma globulin, 0.1% sodium azide, 0.4% BSA and 2% ethylene glycol;
4) a wash solution comprising 50% dimethylsulfoxide in 0.45% NaCl;
5) a diluent buffer comprising 0.1M sodium phosphate (pH 7.5), 0.01% bovine gamma globulin and 0.1% sodium azide;
6) calibrators comprising pooled normal human urine preserved with 0.1% sodium azide with 0.00, 0.50, 1.00, 2.00, 4.00 and 6.00 μg/ml of d,l-amphetamine; and
7) controls comprising pooled normal human urine preserved with 0.1% sodium azide with 0.75 and 5.00 μg/ml of d,l-amphetamine.

All polarized fluorescent measurements were made using the TDx ® Therapeutic Drug Monitoring System which performed the assay in accordance with the following protocol:
1) 25 microliters of standard or unknown test sample were delivered into a predilute well, and a sufficient volume of diluent buffer was added to raise the volume to 500 microliters;
2) a sample from the predilute well (80 μl), 12.5 microliters of pretreatment solution and a diluent buffer (in a quantity sufficient to raise the volume to 1.0 ml) were pipetted into a cuvette, and a background intensity reading was taken;
3) a sample from the predilute well (80 μl), 12.5 microliters of pretreatment solution and 25 microliters each of tracer and antibody were then placed in a cuvette, and a sufficient volume of diluent buffer was added to raise the volume to 2.0 milliliters;
4) the reaction mixture was incubated;
5) the fluorescence polarization due to tracer binding to the antibody was obtained by subtracting the polarized fluorescence intensities of the background from the final polarized fluorescence intensities of the mixture; and
6) the polarization value for the unknown test sample was compared to a standard curve prepared using calibrators of known amphetamine content.

The wash solution was used to rinse the probe of the TDx ® instrument to minimize "carryover", i.e., the adhesion of samples and reagents to the probe. Carryover was determined by assaying an amphetamine solution in normal human urine at 1400 μg/ml followed by a sample of drug-free normal human urine. Percent carryover equals 100×(the measured concentration of amphetamine found in the drug-free urine/the concentration of the amphetamine solution). The percent carryover was determined to be less than or equal to 0.02%. Acceptable carryover was defined as less than 0.05%.

It will be appreciated by one skilled in the art that many of the concepts of the present invention are equally applicable to other types of binding assays. The embodiments described and the alternative embodiments presented are intended as examples rather than as limitations. Thus, the description of the invention is not intended to limit the invention to the particular embodiments disclosed, but it is intended to encompass all equivalents and subject matter within the spirit and scope of the invention as described above and as set forth in the following claims.

What is claimed is:
1. An immunogen comprising a compound of the formula:

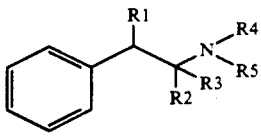

wherein R2, R3, R4, and R5 are selected from the group consisting of X, H, OH and CH$_3$;
wherein X is (M)$_z$WQ wherein
Q is a carrier material,
W is a coupling group selected from the group consisting of NH, CO, COOH, CHO, and OH, present on said carrier material,
z is 0 or 1, and
M is a linking group consisting of from 0 to 15 carbon atoms and heteroatoms, including not more than six heteroatoms, arranged in a straight or branched chain, saturated or unsaturated, with the proviso that not more than two heteroatoms are linked in sequence and that branchings may occur only on carbon atoms, wherein said heteroatoms are selected from the group consisting of nitrogen, oxygen, sulfur, silicon and phosphorus; and
R1 is OCH$_2$CONH-carrier.
2. The immunogen according to claim 1, wherein said carrier is a natural or synthetic substance capable of conferring antigenicity.
3. The immunogen according to claim 2, wherein said carrier is selected from the group consisting of a protein, a glycoprotein, a nucleoprotein, a polypeptide, a polysaccharide, a lipopolysaccharide and a poly(amino acid).
4. The immunogen according to claim 3, wherein said poly(amino acid) carrier is selected from the group consisting of bovine serum albumin, keyhole limpet hemocyanin, egg ovalbumin, bovine gamma-globulin, thyroxine binding globulin and human immunogama-globulin.
5. The immunogen according to claim 1, wherein a plurality of hapten moieties are coupled to said carrier.
6. An immunogen comprising a compound of the formula:

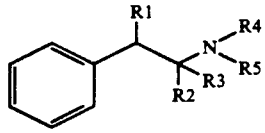

wherein R4 is H and R1, R2, R3, and R5 are selected from the group consisting of X, H, OH and CH$_3$;
wherein X is (M)$_z$WQ wherein
Q is a carrier material,
W is a coupling group selected from the group consisting of NH, CO, COOH, CHO, and OH, present on said carrier material,
z is 0 or 1, and
M is linking group consisting of from 0 to 15 carbon atoms and heteroatoms, including not more than six heteroatoms, arranged in a straight or branched chain, saturated or unsaturated, with the proviso that not more than two heteroatoms are linked in sequence and that branchings may occur only on carbon atoms, wherein said heteroatoms are selected from the group consisting of nitrogen, oxygen, sulfur, silicon and phosphorus.

7. The immunogen of claim 6 wherein R3 is CONH-carrier.

8. The immunogen of claim 6 wherein R5 is selected from the group consisting of CONH-carrier, CH₂CONH-carrier, CH₂CH₂CONH-carrier and CH₂CH=CHCONH-carrier.

9. The immunogen of claim 6 comprising N-carboxymethyl-d,l-amphetamine-BSA:

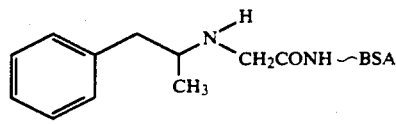

wherein BSA represents the carrier, bovine serum albumin.

* * * * *

UNITED STATES PATENT AND TRADEMARK OFFICE
CERTIFICATE OF CORRECTION

PATENT NO. : 5,101,015
DATED : March 31, 1992
INVENTOR(S) : P. Brynes et al.

Page 1 of 2

It is certified that error appears in the above-identified patent and that said Letters Patent is hereby corrected as shown below:

Column 4, lines 34-39, delete

" 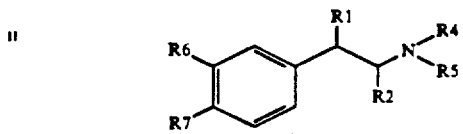 " and insert

-- 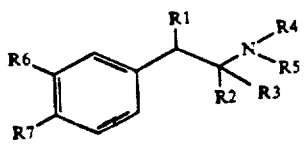 --.

Column 15, lines 12-18, delete

" 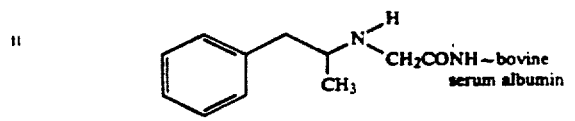 " and insert

-- 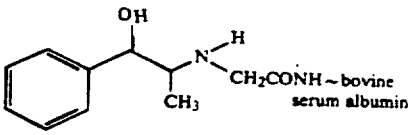 --.

UNITED STATES PATENT AND TRADEMARK OFFICE
CERTIFICATE OF CORRECTION

PATENT NO. : 5,101,015
DATED : March 31, 1992
INVENTOR(S) : P. Brynes, et al.

It is certified that error appears in the above-identified patent and that said Letters Patent is hereby corrected as shown below:

Column 20, lines 16-22, delete "  " and insert

-- 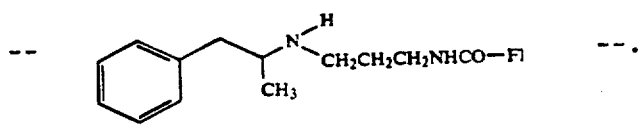 --.

Signed and Sealed this

Fourteenth Day of September, 1993

Attest:

BRUCE LEHMAN

*Attesting Officer*   *Commissioner of Patents and Trademarks*